US011504352B2

(12) United States Patent
Jeong et al.

(10) Patent No.: US 11,504,352 B2
(45) Date of Patent: Nov. 22, 2022

(54) COMPOSITION FOR AMELIORATING CIRCULATORY SYSTEM DISEASES, COMPRISING TEA EXTRACT WITH MODIFIED INGREDIENTS CONTENT

(71) Applicant: Amorepacific Corporation, Seoul (KR)

(72) Inventors: Yeonsu Jeong, Yongin-si (KR); Yong-Deog Hong, Yongin-si (KR); Jeong-Kee Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 57 days.

(21) Appl. No.: 16/760,804

(22) PCT Filed: Oct. 8, 2018

(86) PCT No.: PCT/KR2018/011826
§ 371 (c)(1),
(2) Date: Aug. 31, 2020

(87) PCT Pub. No.: WO2019/088482
PCT Pub. Date: May 9, 2019

(65) Prior Publication Data
US 2020/0397746 A1 Dec. 24, 2020

(30) Foreign Application Priority Data
Oct. 31, 2017 (KR) .......................... 10-2017-0143505

(51) Int. Cl.
*A61K 36/82* (2006.01)
*A61K 31/353* (2006.01)
*A23L 33/105* (2016.01)
*A61P 3/06* (2006.01)
*A61P 9/12* (2006.01)
*A23F 3/16* (2006.01)
*A23L 2/52* (2006.01)
*A61K 9/00* (2006.01)

(52) U.S. Cl.
CPC .............. *A61K 31/353* (2013.01); *A23F 3/16* (2013.01); *A23L 2/52* (2013.01); *A23L 33/105* (2016.08); *A61K 9/0053* (2013.01); *A61K 36/82* (2013.01); *A61P 3/06* (2018.01); *A61P 9/12* (2018.01); *A23V 2002/00* (2013.01); *A61K 2236/333* (2013.01)

(58) Field of Classification Search
None
See application file for complete search history.

(56) References Cited

U.S. PATENT DOCUMENTS

| 6,551,629 B1* | 4/2003 | Gorsek ................ A61K 36/752 424/725 |
| 6,565,896 B1* | 5/2003 | Gorsek ................. A61K 31/16 424/655 |
| 7,763,291 B2 | 7/2010 | Hara et al. |
| 8,697,171 B2 | 4/2014 | Iwasaki et al. |
| 2005/0003026 A1* | 1/2005 | Bok ........................ A23L 27/60 424/736 |
| 2007/0085059 A1* | 4/2007 | Mora-Gutierrez .......................... A61K 31/6615 252/400.21 |
| 2012/0052138 A1 | 3/2012 | Park et al. |

FOREIGN PATENT DOCUMENTS

| JP | 2004-262927 A | 9/2004 |
| JP | 2004-313189 A | 11/2004 |
| JP | 2006-83106 A | 3/2006 |
| JP | 2006-131512 A | 5/2006 |
| JP | 2006-0280385 A | 10/2006 |
| JP | 4728747 B2 | 7/2011 |
| KR | 10-2005-0093894 A | 6/2006 |
| KR | 10-2008-0036411 A | 4/2008 |
| KR | 10-2010-0124519 A | 11/2010 |
| KR | 10-1039145 B1 | 6/2011 |
| KR | 10-2014-0068352 A | 6/2014 |
| WO | 2014/065369 A1 | 5/2014 |

OTHER PUBLICATIONS

Raskin et al. (2004) Current Pharmaceutical Design, 10, 3419-3429. (Year: 2004).*
Revilla et al. (1998) J. Agric. Food Chem. 46, 4592-4597. (Year: 1998).*
Tomonori Nagao et al., "A Green Tea Extract High in Catechins Reduces Body Fat and Cardiovascular Risks in Humans," Obesity, 15(6): 1473-1483 (2007).
Office Action for Korean Patent Application No. 10-2017-0143505 (dated Sep. 8, 2021).
International Search Report from International Application No. PCT/KR2018/011826, dated Jan. 10, 2019.
Written Opinion from International Application No. PCT/KR2018/011826, dated Jan. 10, 2019.
Office Action for Corresponding JP Application No. 2020-523455 (dated May 31, 2022).

* cited by examiner

*Primary Examiner* — Russell G Fiebig
(74) *Attorney, Agent, or Firm* — Merchant & Gould P.C.

(57) ABSTRACT

The present disclosure relates to a composition for ameliorating a circulatory system disease, which contains a green tea extract with modified ingredient content. According to the present disclosure, it is possible to effectively prevent, ameliorate and treat circulatory system diseases without side effects and, thereby, to greatly help patients with circulatory system diseases and contribute to the development of related industries.

8 Claims, 2 Drawing Sheets

COMPOSITION FOR AMELIORATING CIRCULATORY SYSTEM DISEASES, COMPRISING TEA EXTRACT WITH MODIFIED INGREDIENTS CONTENT

This application is a National Stage Application of International Application No. PCT/KR2018/011826, filed Oct. 8, 2018, which claims benefit of Serial No. 10-2017-0143505, filed Oct. 31, 2017 in the Republic of Korea and which applications are incorporated herein by reference. To the extent appropriate, a claim of priority is made to each of the above disclosed applications.

TECHNICAL FIELD

The present disclosure relates to a composition for ameliorating a circulatory system disease, which contains a green tea extract with modified ingredient content.

BACKGROUND ART

Because bloodstream in the body is constantly equilibrated by a complicated and delicate regulatory system, it is not interrupted by hemorrhage, thrombosis, etc. under normal conditions. However, if the state of equilibrium is broken due to several factors, circulatory system diseases may occur due to interrupted blood flow in the blood vessels. Circulatory system diseases are emerging as a major cause of death not only in the US and Europe but also in Korea. In particular, the mortality of arteriosclerotic diseases such as ischemic heart diseases (angina or myocardial infarction) and cerebrovascular diseases is increasing significantly.

Arteriosclerosis is the most representative circulatory system disease. Arteriosclerosis is a very risky disease which causes myocardial infarction or cerebral infarction by causing ischemic state in important organs such as the heart, brain, etc. According to the data published in 2006 by Korea Centers for Disease Control and Prevention, the number of patients who died due to circulatory system diseases such as cerebral hemorrhage, arteriosclerosis, myocardial infarction, etc. was larger than that of cancer. It is though that the reason of the high incidence of these circulatory system diseases is due to the increased prevalence rate of chronic adult diseases such as arteriosclerosis, obesity, diabetes, etc. because of several factors such as westernized eating habits, stresses, etc.

Hyperlipidemia refers to a condition of abnormally elevated levels of cholesterol and triglycerides in the blood. It is known as one of the three risk factors together with hypertension and smoking. Hyperlipidemia is diagnosed when total cholesterol level is 240 mg/dL or higher or when triglyceride level is 200 mg/dL or higher in blood test. Recently, the disease draws a lot of attentions as sudden death occurs frequently in younger generation.

In particular, the circulatory system diseases such as hypertension and hyperlipidemia are considered as the main cause of sudden death, and the number of patients with circulatory system diseases is increasing consistently. In addition, because the number of patients is increasing in the elderly, the importance of preparation and management is increasing with the extended life span and the entry into the aging era.

Although many researches have been conducted for treatment of the circulatory system diseases, the studies on effective natural product-derived substances with few side effects have been unsatisfactory.

DISCLOSURE

Technical Problem

The present disclosure is directed to providing a natural product-derived composition for ameliorating a circulatory system disease, which provides excellent effect with very few side effects.

Technical Solution

The present disclosure provides a composition for preventing or ameliorating a circulatory system disease, which contains a tea extract.

In particular, the present disclosure provides a composition for preventing or ameliorating a circulatory system disease, which contains a green tea extract containing 8-25 wt % of (−)-gallocatechin gallate (GCG), 1-8 wt % of (−)-catechin gallate (CG) and 7-15 wt % of (−)-epigallocatechin gallate (EGCG), based on the total weight of the composition, as an active ingredient.

Advantageous Effects

According to the present disclosure, it is possible to effectively prevent, ameliorate and treat circulatory system diseases without side effects through various effects on blood vessels and, thereby, to greatly help patients with circulatory system diseases and contribute to the development of related industries.

BEST MODE

Figure 1:
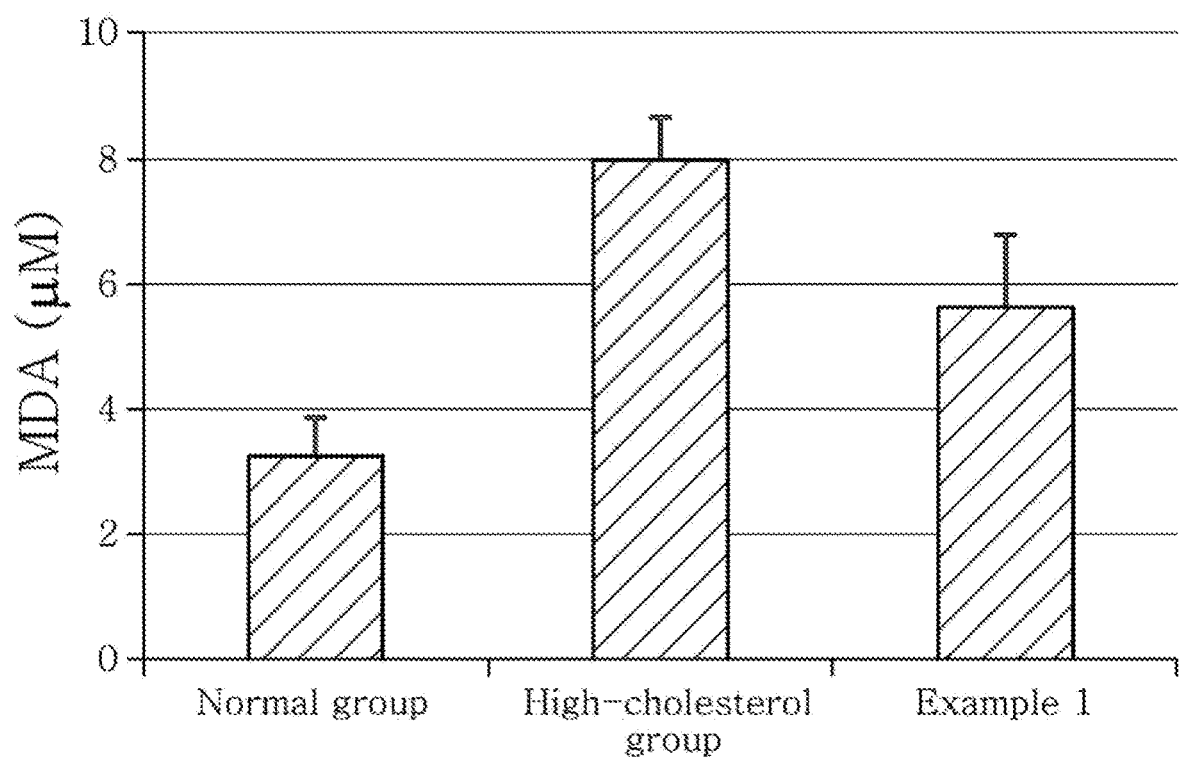
FIG. 1 shows that an extract according to an aspect of the present disclosure effectively decreases lipid peroxide in blood.

In the present disclosure, a "green tea extract" includes one extracted from tea (*Camellia sinensis*), which is an evergreen shrub belonging to the family Theaceae, regardless of extraction method, extraction solvent, extracted ingredients or extract type. The term also includes a fraction obtained by fractionating the extract with a specific solvent. The tea includes one or more selected from a group consisting of the leaf, flower, stem, fruit and root of tea tree. Specifically, it may be leaf. Specifically, the extract may be in powder form. The extraction or fractionation may be conducted using water, an organic solvent or a mixed solvent thereof. The organic solvent may be an alcohol, acetone, hexane, ethyl acetate, carbon dioxide, or a mixed solvent of two or more of them, although not being limited thereto. The extraction or fractionation may be conducted at room temperature or under heating under a condition where the active ingredients of green tea are not destroyed or the destruction is minimized. The alcohol may be a $C_1$-$C_5$ lower alcohol. The number or method of the extraction or fractionation is not particularly limited. For example, cold extraction, ultrasonic extraction, reflux condensation extraction, hot water extraction, etc. may be used. Specifically, after extracting or fractionating active ingredients at room temperature or under heating and filtering the resultant, the green tea extract of the present disclosure may be obtained by concentrating the filtrate under reduced pressure.

In the present disclosure, "total epicatechin" includes (−)-epigallocatechin (EGC), (−)epicatechin (EC), (−)-epigallocatechin gallate (EGCG) and (−)-epicatechin 3-O-gallate (ECG).

In the present disclosure, the "circulatory system disease" refers to a disease caused by the disorder of the circulatory system, i.e., the heart, arteries and veins, and includes heart diseases such as heart failure, angina, myocardial infarction, etc., arteriosclerosis, hyperlipidemia, hypercholesterolemia, hypertension, stroke and thrombosis.

In the present disclosure, "oxidative stress" refers to the side effect of reactive oxygen species. The human body regulates the amount of reactive oxygen species on its own. If the production of reactive oxygen species is increased rapidly or if the function of removing them declines due to several reasons, a variety of diseases are induced by the reactive oxygen species. The side effect caused by the reactive oxygen species is called oxidative stress. If the reactive oxygen species are produced excessively and oxidative stress is accumulated consistently, genes in cells are negatively affected or damaged. For example, reactive oxygen species excessively produced by $H_2O_2$ become unstable because they have free radicals and, thus, have powerful reactivity. Therefore, they destroy cellular homeostasis and kill cells by oxidizing proteins, lipids, etc. in the cells.

In the present disclosure, "pharmaceutically acceptable" means that use of a general medicinal dosage avoids a significant toxic effect and thus can be accepted or is accepted as appropriate in application to animals, particularly to human, by the government or a corresponding regulatory organization, or is listed in the pharmacopeia or regarded as described in general pharmacopeia.

In the present disclosure, a "pharmaceutically acceptable salt" means a salt according to an aspect of the present disclosure that is pharmaceutically acceptable and has the desired pharmacological activity of a parent compound.

If lipids such as cholesterol are increased in blood, they are accumulated gradually on the blood vessel walls. As a result, the blood vessel walls become thicker, the blood vessels become narrower, and blood clots are formed at the site where the lipids are accumulated. Arteriosclerosis is a cardiovascular disease caused by such thickening of blood vessel walls and narrowing of blood vessels. It is one of the main causes of sudden death. Arteriosclerosis begins as vascular endothelial cells are stimulated by various oxidative stresses and inflammatory factors. Due to these stimuli, the blood vessel wall becomes loose and fatty streaks are formed as lipids are accumulated excessively. Meanwhile, foam cells are formed as lipid peroxides produced in blood are taken up by macrophages. The foam cells play an important role in the development of arteriosclerosis. Hence, for prevention of arteriosclerosis, it is important to prevent oxidative stresses and inhibit lipid production. Thus, in an aspect, the present disclosure seeks a composition which exhibits higher effect than the existing green tea hot water extract.

In an aspect, the present disclosure may provide a composition for preventing or ameliorating a circulatory system disease, which contains a green tea extract containing 8-25 wt % of (−)-gallocatechin gallate (GCG), 1-8 wt % of (−)-catechin gallate (CG) and 7-15 wt % of (−)-epigallocatechin gallate (EGCG), based on the total weight of the composition, as an active ingredient.

In another aspect, the present disclosure may provide a composition for improving blood circulation or improving blood lipids, which contains a green tea extract containing 8-25 wt % of (−)-gallocatechin gallate (GCG), 1-8 wt % of (−)-catechin gallate (CG) and 7-15 wt % of (−)-epigallocatechin gallate (EGCG), based on the total weight of the composition, as an active ingredient. In an exemplary embodiment, the lipid may be cholesterol.

In another aspect, the present disclosure may relate to a method for preventing or ameliorating a circulatory system disease, which includes administering a composition containing a green tea extract containing 8-25 wt % of (−)-gallocatechin gallate (GCG), 1-8 wt % of (−)-catechin gallate (CG) and 7-15 wt % of (−)-epigallocatechin gallate (EGCG), based on the total weight of the composition, as an active ingredient, to an individual.

In another aspect, the present disclosure may relate to a use of a green tea extract containing 8-25 wt % of (−)-gallocatechin gallate (GCG), 1-8 wt % of (−)-catechin gallate (CG) and 7-15 wt % of (−)-epigallocatechin gallate (EGCG) for preparing a composition for preventing or ameliorating a circulatory system disease.

In another aspect, the present disclosure may relate to a method for improving blood circulation or improving blood lipids, which includes administering a composition containing a green tea extract containing 8-25 wt % of (−)-gallocatechin gallate (GCG), 1-8 wt % of (−)-catechin gallate (CG) and 7-15 wt % of (−)-epigallocatechin gallate (EGCG), based on the total weight of the composition, as an active ingredient, to an individual.

In another aspect, the present disclosure may relate to a use of a green tea extract containing 8-25 wt % of (−)-gallocatechin gallate (GCG), 1-8 wt % of (−)-catechin gallate (CG) and 7-15 wt % of (−)-epigallocatechin gallate (EGCG) for preparing a composition for improving blood circulation or improving blood lipids.

In an aspect, the GCG may be contained in an amount of 8 wt % or more, 9 wt % or more, 10 wt % or more, 11 wt % or more, 12 wt % or more, 12.52 wt % or more, 13 wt % or more, 14 wt % or more, 16 wt % or more, 18 wt % or more, 20 wt % or more, 22 wt % or more, or 24 wt % or more, based on the total weight of the composition or the extract. In another aspect, the GCG may be contained in an amount of 25 wt % or less, 23 wt % or less, 21 wt % or less, 19 wt % or less, 17 wt % or less, 15 wt % or less, 14 wt % or less, 13 wt % or less, 12.55 wt % or less, 12 wt % or less, 11 wt % or less, 10 wt % or less, or 9 wt % or less, based on the total weight of the composition or the extract.

In an aspect, the CG may be contained in an amount of 1 wt % or more, 2 wt % or more, 2.3 wt % or more, 2.38 wt % or more, 3 wt % or more, 4 wt % or more, 5 wt % or more, 6 wt % or more, or 7 wt % or more, based on the total weight of the composition or the extract. In another aspect, the CG may be contained in an amount of 8 wt % or less, 7 wt % or less, 6 wt % or less, 5 wt % or less, 4 wt % or less, 3 wt % or less, 2.5 wt % or less, 2.3 wt % or less, or 2 wt % or less, based on the total weight of the composition or the extract.

In an aspect, the EGCG may be contained in an amount of 7 wt % or more, 8 wt % or more, 8.48 wt % or more, 8.5 wt % or more, 9 wt % or more, 10 wt % or more, 12 wt % or more, or 14 wt % or more, based on the total weight of the composition or the extract. In another aspect, the EGCG may be contained in an amount of 15 wt % or less, 13 wt % or less, 11 wt % or less, 10 wt % or less, 9 wt % or less, 8.5 wt % or less, 8.48 wt % or less, 8.3 wt % or less, 8 wt % or less, or 7.5 wt % or less, based on the total weight of the composition or the extract.

In another exemplary embodiment, the catechin content in the extract may be 25 wt % or less based on the total weight of the composition or the extract. In an aspect, the catechin content may be 25 wt % or less, 20 wt % or less, 18 wt % or less, 16 wt % or less, 15 wt % or less, 14 wt % or less, 12 wt % or less, 10 wt % or less, 8 wt % or less, 6 wt % or less, or 4 wt % or less, based on the total weight of the composition or the extract. In another aspect, the catechin content may be 3 wt % or more, 6 wt % or more, 8 wt % or more, 10 wt % or more, 12 wt % or more, 13 wt % or more, 14 wt % or more, 16 wt % or more, 18 wt % or more, 20 wt % or more, or 24 wt % or more, based on the total weight of the composition or the extract.

In another exemplary embodiment, the total epicatechin content in the extract may be 20 wt % or less based on the total weight of the composition or the extract. In an aspect, the total epicatechin content may be 20 wt % or less, 18 wt % or less, 16 wt % or less, 15 wt % or less, 14 wt % or less, 12 wt % or less, 10 wt % or less, 8 wt % or less, 6 wt % or less, or 4 wt % or less, based on the total weight of the composition or the extract. In another aspect, the epicatechin content may be 3 wt % or more, 6 wt % or more, 8 wt % or more, 10 wt % or more, 12 wt % or more, 13 wt % or more, 14 wt % or more, 16 wt % or more, or 18 wt % or more, based on the total weight of the composition or the extract.

In another exemplary embodiment, the sum of the contents of GCG and CG in the composition or the extract may be 11-25 wt % based on based on the total weight of the composition or the extract. In an aspect, the sum of the contents of GCG and CG may be 11 wt % or more, 12 wt % or more, 13 wt % or more, 14 wt % or more, 14.5 wt % or more, 15 wt % or more, 16 wt % or more, 18 wt % or more, 20 wt % or more, 22 wt % or more, or 24 wt % or more, based on based on the total weight of the composition or the extract. In another aspect, the sum of the contents of GCG and CG may be 25 wt % or less, 23 wt % or less, 21 wt % or less, 19 wt % or less, 17 wt % or less, 16 wt % or less, 15 wt % or less, 14.5 wt % or less, 14 wt % or less, 13 wt % or less, or 12 wt % or less, based on based on the total weight of the composition or the extract.

If the content of each ingredient is outside the above-described ranges, the effect described in the present disclosure may be insignificant or similar to that of the general green tea extract.

In an aspect, the extract may be one extracted with one or more selected from a group consisting of water, a $C_1$-$C_6$ alcohol and a mixture thereof once or multiple times. In an exemplary embodiment, the alcohol may be ethanol.

In another aspect, the concentration of the alcohol in the mixture may be 40% (v/v) or higher, 50% (v/v) or higher, 60% (v/v) or higher, or 65% (v/v) or higher. In another aspect, the concentration may be 70% (v/v) or lower, 65% (v/v) or lower, 60% (v/v) or lower, 50% (v/v) or lower, or 45% (v/v) or lower. If the concentration is outside the above range, the active ingredients may not be extracted sufficiently or the extracted active ingredients may be denatured.

In an aspect, the content of the extract in the composition may be 1-100 wt % based on dry weight. In an exemplary embodiment, the content of the extract in the composition may be 1 wt % or more, 10 wt % or more, 20 wt % or more, 30 wt % or more, 40 wt % or more, 50 wt % or more, 60 wt % or more, 70 wt % or more, 80 wt % or more, or 90 wt % or more, based on dry weight. In another exemplary embodiment, the content of the extract in the composition may be 100 wt % or less, 90 wt % or less, 80 wt % or less, 70 wt % or less, 60 wt % or less, 50 wt % or less, 40 wt % or less, 30 wt % or less, or 20 wt % or less, based on dry weight.

In another aspect, the composition may be administered orally.

In an exemplary embodiment, the administration dosage of the active ingredient may be 5-1000 mg/kg/day based on dry weight. In an aspect, the administration dosage may be 5 mg/kg/day or more, 100 mg/kg/day or more, 200 mg/kg/day or more, 300 mg/kg/day or more, 400 mg/kg/day or more, 500 mg/kg/day or more, 600 mg/kg/day or more, 700 mg/kg/day or more, 800 mg/kg/day or more, or 900 mg/kg/day or more. In another aspect, the administration dosage may be 1000 mg/kg/day or less, 900 mg/kg/day or less, 800 mg/kg/day or less, 700 mg/kg/day or less, 600 mg/kg/day or less, 500 mg/kg/day or less, 400 mg/kg/day or less, 300 mg/kg/day or less, 200 mg/kg/day or less, 100 mg/kg/day or less, 50 mg/kg/day or less, or 10 mg/kg/day or less.

In another exemplary embodiment, the circulatory system disease may be one or more selected from a group consisting of arteriosclerosis, hyperlipidemia, hypercholesterolemia, hypertension and thrombosis.

In another exemplary embodiment, the circulatory system disease may be caused by one or more selected from a group consisting of excessive lipid peroxide production, excessive cholesterol production, fatty streak formation, thrombosis, decreased blood vessel diameter or volume, increased blood pressure, impaired blood circulation, and vasoconstriction.

In another exemplary embodiment, the circulatory system disease may be caused by one or more selected from a group consisting of increased free radical production, increased amount or activity of HMG-CoA reductase, increased amount or activity of angiotensin-converting enzyme, and decreased nitric oxide production in vascular endothelial cells.

The circulatory system diseases such as arteriosclerosis, hyperlipidemia, hypercholesterolemia, hypertension and thrombosis are diseases caused by increased free radical production, increased amount or activity of HMG-CoA reductase, increased amount or activity of angiotensin-converting enzyme, excessive lipid peroxide production due to decreased nitric oxide production in vascular endothelial cells, excessive cholesterol production, fatty streak formation, thrombosis, decreased blood vessel diameter or volume, increased blood pressure, impaired blood circulation, vasoconstriction, etc.

Among the circulatory system diseases, arteriosclerosis is a diseased characterized by disorder of lipid metabolism, inflammation of blood vessels, and formation of arterial blood clots. In particular, the formation of arterial blood clots leads to acute/chronic complications of arteriosclerosis and is known as a major risk factor causing hypertension, myocardial infarction and stroke. Blood platelets are main components of the arterial blood clots and they are also known to be involved in the formation and development of arteriosclerotic plaques.

Increased cholesterol and lipid levels in blood often lead to arteriosclerosis or hyperlipidemia, and interrupted bloodstream due to arteriosclerosis, hyperlipidemia and hypercholesterolemia can cause heart failure, stroke, etc. Due to surplus nutrient intake by modern people, excessive cholesterol remains after satisfying the cellular requirement. The cholesterol is transported in the form of a low-density lipoprotein (LDL) and is adsorbed to the vascular endothelium. It is also converted to foam cells, fatty streaks or atheroma, which cause arteriosclerosis, coronary artery disease, stroke, peripheral arterial contraction, hypertension, etc. by lowering vasoconstriction and vasodilation abilities. The foam cells destroy or thicken blood vessel walls through repeated inflammatory response and cellular growth, leading to blood clot formation by platelets. Consequently, this process leads to contraction of blood vessels due to arteriosclerosis and obstruction of blood vessels due to thrombosis.

Since the extract and the composition according to an aspect of the present disclosure exhibit the effects of inhibiting free radical production, decreasing the amount or activity of HMG-CoA reductase, decreasing the amount or activity of angiotensin-converting enzyme, decreasing nitric oxide production in vascular endothelial cells, etc., inhibition of lipid peroxide production, inhibition of cholesterol production, inhibition of fatty streak formation, inhibition of blood clot formation, increase in blood vessel diameter or volume, decreased in blood pressure, improvement of blood circulation, vasodilation, etc. may be achieved therethrough. As a result, circulatory system diseases such as arteriosclerosis, hyperlipidemia, hypercholesterolemia, hypertension, stroke and thrombosis may be prevented, treated and ameliorated effectively.

The composition may be a food or pharmaceutical composition.

The formulation of the food composition is not particularly limited. For example, it may be prepared into a tablet, a granule, a pill, a powder, a liquid such as a drink, a caramel, a gel, a bar, a tea bag, etc. The food composition of each formulation may further contain, in addition to the active ingredient, ingredients commonly used in the art depending on the particular formulation or purpose of use, which may be adequately selected by those skilled in the art. In this case, a synergistic effect may be achieved. In addition, the food composition may be a health functional food composition.

The composition may be administered in various ways, including simple intake, drinking, injection, spraying, squeezing, etc.

For the food composition according to an aspect of the present disclosure, the administration dosage of the active ingredient may be determined within the level of those skilled in the art, and may vary depending on various factors such as the age and health condition of a subject, presence of complication(s), etc.

The food composition according to an aspect of the present disclosure may be, for example, various foods such as chewing gum, caramel, candy, ices, confectionery, etc., drinks such as soft drinks, mineral water, alcoholic beverages, etc., or health functional food products including multivitamins, minerals, etc.

In addition, the food composition according to an aspect of the present disclosure may further contain various nutrients, vitamins, minerals (electrolytes), flavors including synthetic flavors and natural flavors, colorants, extenders (cheese, chocolate, etc.), pectic acid and its salts, alginic acid and its salts, organic acids, protective colloidal thickeners, pH control agents, stabilizers, antiseptics, glycerin, alcohols, carbonating agents used in carbonated drinks, etc. In addition, the food composition according to an aspect of the present disclosure may contain a pulp for preparing natural fruit juice, fruit juice drinks and vegetable drinks. These ingredients may be used either independently or in combination. Although the proportion of these additives is of no great importance, they may be generally contained within a range of about 0-60 parts by weight based on 100 parts by weight of the composition according to an aspect of the present disclosure.

The pharmaceutical composition according to an aspect of the present disclosure may be administered orally, parenterally, rectally, topically, transdermally, intravenously, intramuscularly, intraperitoneally, subcutaneously, etc. A formulation for oral administration may be a tablet, a pill, a soft or hard capsule, a granule, a powder, a fine granule, a liquid, an emulsion or a pellet, although not being limited thereto. A formulation for parenteral administration may be a solution, a suspension, an emulsion, a gel, an injection, a medicinal drop, a suppository, a patch or a spray, although not being limited thereto. These formulations may be prepared easily according common methods in the art and may further contain a surfactant, an excipient, a wetting agent, an emulsification accelerator, a suspension, a salt or buffer for control of osmotic pressure, a colorant, a flavor, a stabilizer, an antiseptic, a preservative or other commonly used adjuvants.

The composition according to an aspect of the present disclosure may contain a pharmaceutically acceptable salt. The salt may include: (1) an acid addition salt formed from an inorganic acid such as hydrochloric acid, hydrobromic acid, sulfuric acid, nitric acid, phosphoric acid, etc., or from an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid and muconic acid; or (2) a salt formed as the acidic proton present in the parent compound is replaced.

The application amount or administration dosage of the pharmaceutical composition according to an aspect of the present disclosure will vary depending on the age, sex and body weight of a subject to be treated, pathological condition and severity thereof, administration route and the discretion of a diagnoser. The determination of the administration dosage of the active ingredient based on these factors is within the level of those skilled in the art.

Hereinafter, the present disclosure will be described in detail through examples, comparative examples, experimental examples and formulation examples. However, these examples are provided only to help understanding of the present disclosure and the scope of the present disclosure is not limited by the examples.

[Example 1] Preparation of Green Tea Extract with Modified Ingredient Content

After adding 1000 mL of 50% ethanol to 100 g of green tea (*Camellia sinensis*, Osulloc Farm, Jeju, Korea), the mixture was refluxed at 60° C. for 1 hour under stirring.

After cooling the sample to room temperature, a solution obtained by filtering the same was distilled under reduced pressure (to remove the ethanol). 23 g of an extract was obtained as a dark brown powder (yield 23%). Then, 10 g of the obtained sample 1 was dissolved in 90 mL of water and stirred at 80° C. for 30 minutes to 8 hours. After cooling to room temperature and filtering insoluble materials, 10 g of a thermally aged green tea extract was obtained by concentrating under reduced pressure. For the thermally aged green tea extracts obtained by varying the stirring time, the content of GCG, etc. was measured using an apparatus described in Table 1. After identifying the time when the content of GCG was the highest, 10 g of a thermally aged green tea extract (GT-LE-10GCG, Example 1, sample 2) was obtained by stopping stirring at that time.

The composition of the obtained extract was analyzed under the condition described in Table 1, and the composition analysis result for different stirring time is given in Table 2. The composition of the extract was different from that of the existing green tea extract. Specifically, it contained 8-25 wt % of (−)-gallocatechin gallate (GCG), 1-8 wt % of (−)-catechin gallate (CG) and 7-15 wt % of (−)-epigallocatechin gallate (EGCG). At the time when the content of the GCG was 10-13 wt %, the contents of EGCG and CG were 8-10 wt % and 1-3 wt %, respectively.

TABLE 1

| Composition analysis condition | |
|---|---|
| Column | Sun fire C18 5 μm, 4.6 × 250 mm |
| Detector | UV 280 nm |
| Apparatus | Waters 2998 PDA detector, Waters 1525 pump, Waters 2707 autosampler |
| Dilution | Gradient |
| | A: water with 0.1% TFA (trifluoroacetic acid) |
| | B: acetonitrile |
| Gradient profile | 0 min A (95): B (5) |
| | 1 min A (95): B (5) |
| | 20 min A (71): B (29) |
| | 22 min A (71): B (29) |
| Flow rate | 1 mL/min |
| Injection volume | 20 μL |

TABLE 2

| Stirring time | EGCG | GCG | ECG | CG |
|---|---|---|---|---|
| 1 hour | 11.79 | 7.6 | 1.16 | 1.16 |
| 3 hours | 9.67 | 11.08 | 2.44 | 1.46 |
| 5 hours | 8.48 | 12.52 | 1.9 | 2.38 |
| 7 hours | 6.71 | 9.44 | 1.85 | 1.56 |

[Comparative Example 1] Preparation of General Green Tea Extract (Green Tea Extract Notified by the Ministry of Food and Drug Safety)

After adding 1000 mL of water to 100 g of green tea (*Camellia sinensis*, Osulloc Farm, Jeju, Korea), the mixture was refluxed at 80° C. for 1 hour under stirring. After cooling the sample to room temperature, a solution obtained by filtering the same was distilled under reduced pressure. As a result, 0.29 g of a green tea extract (Comparative Example 1) was obtained as a dark brown powder (yield 29%).

Composition analysis was conducted in the same manner as Example 1. The composition of the extract prepared according to Example 1 with a stirring time of 4-5 hours was compared to that of the general green tea extract of Comparative Example 1. The result is given in Table 3.

TABLE 3

| | Example 1 | Comparative Example 1 |
|---|---|---|
| EGCG | 8.3 | 12.8 |
| EGC | 3.9 | 6.7 |
| ECG | 1.8 | 1.8 |
| EC | 1.2 | 2.0 |
| Total epicatechin | 15.2 | 23.3 |

In Table 2 and Table 3, EGC is (−)-epigallocatechin, EC is (−)-epicatechin, and ECG is (−)-epicatechin 3-O-gallate.

In Table 2 and Table 3, all the units are wt % based on the total weight of the extract.

[Experimental Example 1] Comparison of Antioxidant Activity

The difference in the antioxidant activity of the extract depending on the preparation method was compared.

DPPH (2,2-diphenyl-1-picrylhydrazyl) is a violet free radical compound which is very stable on its own and exhibits characteristic light absorption. After adding a 100 μM DPPH ethanol solution to the extracts of Example 1 and Comparative Example 1 and conducting reaction at 37° C. for 30 minutes, free radical scavenging activity was evaluated by measuring absorbance at 515 nm.

The result is given in Table 4. It was confirmed that the extract of Example 1 has much higher antioxidant activity than the extract of Comparative Example 1.

TABLE 4

| | % inhibition | | | | | | | | |
|---|---|---|---|---|---|---|---|---|---|
| Concentration (μg/mL) | 40 | 20 | 10 | 5 | 2.5 | 1.25 | 0.63 | 0.31 | $IC_{50}$ (μg/mL) |
| Example 1 | 92.7 | 92.4 | 72.4 | 45.9 | 28.2 | 14.7 | 8.5 | 3.9 | 4.4 ± 0.1 |
| Comparative Example 1 | 94.6 | 40.8 | 21.9 | 10.7 | 5.5 | 2.6 | 1.5 | 0.5 | 13.6 ± 2.3 |

[Experimental Example 2] Evaluation of
HMG-CoA Reductase
(3-hydroxy-3-methyl-glutaryl-CoA Reductase or
HMGR) Inhibiting Effect The inhibitory effect against HMGR, which is a major enzyme in cholesterol synthesis, was evaluated. The inhibitory effect against this enzyme was evaluated by measuring the change in absorbance caused by decrease of NADPH required for conversion of HMG-CoA to mevalonate and coenzyme A. After mixing the extracts of Example 1 and Comparative Example 1 (30 μg/mL each) with HMGR and adding a buffer containing HMG-CoA and NADPH, absorbance was measured at 340 nm with 2-minute intervals. A commercially available apparatus was used for the experiment.

The result is given in Table 5. It can be seen that the extract of Example 1 can significantly inhibit the cholesterol-synthesizing enzyme unlike the extract of Comparative Example 1.

TABLE 5

|  | Example 1 | Comparative Example 1 |
| --- | --- | --- |
| HMGR inhibition (%) | 88.2 | <5 |

[Experimental Example 3] Inhibition of Lipid
Peroxide Production Induced by High-Cholesterol
Diet For the extract of Example 1, the effect of inhibiting lipid peroxide production induced by a high-cholesterol diet was evaluated.

Specifically, 10-week-old male guinea pigs weighing about 550 g were divided into a group fed with a normal feed, a group fed with a high-cholesterol feed (containing 1 wt % of cholesterol and 10 wt % of coconut oil based on total feed weight) and a group fed with the high-cholesterol feed to which 0.15 wt % of the extract of Example 1 was added based on total feed weight. The animals were fed for 8 weeks and blood was taken after fasting on the last day.

After adding thiobarbituric acid to malondialdehyde (MDA) produced as lipid peroxides in blood plasma were degraded by a sodium dodecyl sulfate buffer and conducting reaction at 95° C. for 1 hour, the production of TBARS (thiobarbituric acid reactive substances) was quantified by measuring fluorescence at an excitation wavelength of 540 nm and an emission wavelength of 590 nm. A commercially available apparatus was used for the quantification of lipid peroxides.

The result is shown in FIG. 1. It can be seen that the amount of lipid peroxides in blood was significantly decreased in the group fed with the high-cholesterol feed to which the extract of Example 1 was added, as compared to the group fed with the high-cholesterol feed.

[Experimental Example 4] Evaluation of
Angiotensin-Converting Enzyme (ACE) Inhibiting
Effect Angiotensin-converting enzyme (ACE) is an enzyme which converts angiotensin I to the active vasoconstrictor angiotensin II, and is a major target enzyme of blood pressure-lowering drugs. The effect of inhibiting the enzyme was evaluated by measuring the amount of 3-hyroxybutylic acid (3HB) produced from the reaction between the extracts of Example 1 and Comparative Example 1 with ACE and the substrate 3-hydroxybutylyl-Gly-Gly-Gly from the change in absorbance at 450 nm owing to the decrease in NADH required for the reaction. A commercially available apparatus was used for the experiment.

As seen from Table 6, it can be seen that the extract of Example 1 exhibits significantly higher ACE inhibiting effect than the extract of Comparative Example 1.

TABLE 6

|  | % inhibition | |
| --- | --- | --- |
| Concentration (μg/mL) | 100 | 50 |
| Example 1 | 69.7 | 41.8 |
| Comparative Example 1 | 35.2 | 22.3 |

[Experimental Example 5] Evaluation of Increased
Production of Vasodilator Nitric Oxide (NO)

Nitric oxide which is produced by endothelial nitric oxide synthase (eNOS) in vascular endothelial cells is an important physiologically active factor which promotes blood circulation and lowers blood pressure by dilating blood vessels. After treating human umbilical vein endothelial cells (HUVECs) with the extracts of Example 1 and Comparative Example 1, the increased amount of nitric oxide 3 hours and 6 hours later was evaluated using a Griess reagent prepared by mixing a 0.2% naphthylethylenediamine (Sigma, USA) aqueous solution and a 5% phosphoric acid solution of 2% sulfanilamide (Sigma, USA) by measuring absorbance at 550 nm.

Figure 2:
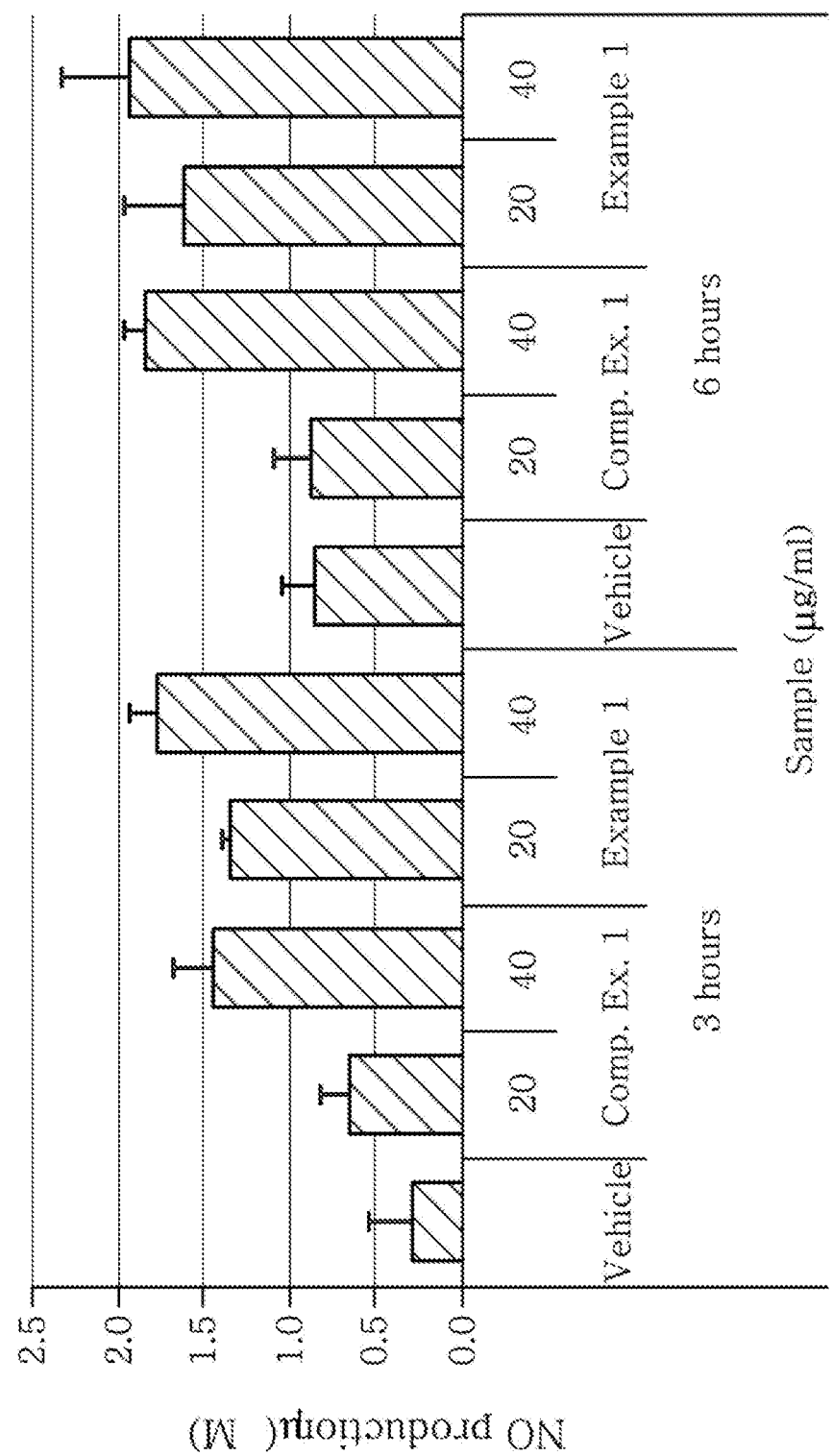
FIG. 2 shows that an extract according to an aspect of the present disclosure remarkably increases nitric oxide production in vascular endothelial cells.

As seen from FIG. 2, the NO production was increased both for Comparative Example 1 and Example 1 as compared to a vehicle group treated with the same solvent only, and Example 1 showed about 2 times more NO production than Comparative Example 1.

[Formulation Example 1] Soft Capsule

A soft capsule filling solution was prepared by mixing 150 mg of the extract of Example 1 with 440 mg of lactose, 430 mg of corn starch and 2 mg of magnesium stearate. Then, after preparing a soft capsule sheet by mixing 66 parts by weight of gelatin, 24 parts by weight of glycerin and 10 parts by weight of sorbitol solution separately from this, a soft capsule was prepared by filling with the filling solution.

[Formulation Example 2] Tablet

After mixing 150 mg of the extract of Example 1 with 15 mg of vitamin E, 15 mg of vitamin C, 250 mg of galactooligosaccharide, 60 mg of lactose and 140 mg of maltose and granulating the mixture using a fluidized-bed dryer, 8 mg of sugar ester was added. A tablet was prepared by tableting the granule.

[Formulation Example 3] Drink

After mixing 80 mg of the extract of Example 1 with 9 mg of vitamin E, 9 mg of vitamin C, 10 g of glucose, 0.6 g of citric acid and 25 g of oligosaccharide syrup, 400 mL of purified water was added. After filling the mixture in a bottle, a drink was prepared by sterilizing at 30° C. for 4-5 seconds.

[Formulation Example 4] Granule

After mixing 150 mg of the extract of Example 1 with 9 mg of vitamin E, 9 mg of vitamin C, 250 mg of anhydrous crystalline glucose and 550 mg of starch and forming the mixture into a granule using a fluidized-bed granulator, the prepared granule was filled in a pouch.

[Formulation Example 5] Health Food

A health food was prepared by mixing 150 mg of the extract of Example 1 with a vitamin mixture (70 μg of vitamin A acetate, 1.0 mg of vitamin E, 0.13 mg of vitamin 0.15 mg of vitamin $B_2$, 0.5 mg of vitamin $B_6$, 0.2 μg of vitamin $B_{12}$, 10 mg of vitamin C, 10 μg of biotin, 1.7 mg of nicotinamide, 50 μg of folic acid) and a mineral mixture (1.75 mg of ferrous sulfate, 0.82 mg of zinc oxide, 25.3 mg of magnesium carbonate, 15 mg of potassium monophosphate, 55 mg of calcium diphosphate, 90 mg of potassium citrate, 100 mg of calcium carbonate, 24.8 mg of magnesium chloride).

[Formulation Example 6] Health Drink 900 mL of a health drink was prepared by mixing 50 mg of the extract of Example 1 with 1000 mg of citric acid, 100 g of oligosaccharide, 2 g of plum concentrate, 1 g of taurine and purified water as balance.

While the exemplary embodiments have been shown and described, it will be understood by those skilled in the art that various changes in form and details may be made thereto without departing from the spirit and scope of this disclosure as defined by the appended claims. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A method for ameliorating a circulatory system disease, the method comprising: administering, to a subject, a composition containing a green tea extract comprising 8-25 wt % of (−)-gallocatechin gallate (GCG), 1-8 wt % of (−)-catechin gallate (CG) and 7-15 wt % of (−)-epigallocatechin gallate (EGCG), based on the total weight of the composition, as an active ingredient,
wherein the total epicatechin content in the extract is 20 wt % or less based on the total weight of the composition, wherein the circulatory system disease is one or more selected from a group consisting of arteriosclerosis, hyperlipidemia, and hypercholesterolemia,
wherein the extract is one extracted with a mixture of water and C1-C6 alcohol once or multiple times, and wherein the concentration of the alcohol in the mixture is 40-60% (v/v).

2. The method according to claim 1, wherein the sum of the contents of GCG and CG in the extract is 11-25 wt % based on the total weight of the composition.

3. The method according to claim 1, wherein the content of the extract in the composition is 1-100 wt % based on dry weight.

4. The method according to claim 1, wherein the composition is administered orally.

5. The method according to claim 1, wherein the administration dosage of the active ingredient is 5-1000 mg/kg/day based on dry weight.

6. The method according to claim 1, wherein the circulatory system disease is caused by one or more selected from a group consisting of excessive lipid peroxide production, excessive cholesterol production, fatty streak formation, thrombosis, decreased blood vessel diameter or volume, increased blood pressure, impaired blood circulation, and vasoconstriction.

7. The method according to claim 1, wherein the circulatory system disease is caused by one or more selected from a group consisting of increased free radical production, increased amount or activity of HMG-CoA reductase, increased amount or activity of angiotensin-converting enzyme, and decreased nitric oxide production in vascular endothelial cells.

8. The method according to claim 1, wherein the composition is a food or pharmaceutical composition.

* * * * *